US009028463B2

(12) United States Patent
Nozaki et al.

(10) Patent No.: US 9,028,463 B2
(45) Date of Patent: May 12, 2015

(54) MICRONEEDLE DEVICE, AND METHOD FOR ENHANCING THE EFFICACY OF INFLUENZA VACCINE BY USING MICRONEEDLE DEVICE

(75) Inventors: Chikateru Nozaki, Kikuchi (JP); Kazuyoshi Kaminaka, Kikuchi (JP); Junichi Matsuda, Kikuchi (JP); Takaaki Terahara, Tsukuba (JP); Tetsuji Kuwahara, Tsukuba (JP); Seiji Tokumoto, Tsukuba (JP)

(73) Assignees: Hisamitsu Pharmaceutical Co., Inc., Saga (JP); The Chemo-Sero-Therapeutic Research Institute, Kumamoto (JP)

( * ) Notice: Subject to any disclaimer, the term of this patent is extended or adjusted under 35 U.S.C. 154(b) by 130 days.

(21) Appl. No.: 13/001,995

(22) PCT Filed: May 22, 2009

(86) PCT No.: PCT/JP2009/059452
§ 371 (c)(1),
(2), (4) Date: Dec. 29, 2010

(87) PCT Pub. No.: WO2010/001671
PCT Pub. Date: Jan. 7, 2010

(65) Prior Publication Data
US 2011/0112509 A1    May 12, 2011

(30) Foreign Application Priority Data

Jun. 30, 2008  (JP) .................................. 2008-170220
Oct. 16, 2008  (JP) .................................. 2008-267322

(51) Int. Cl.
*A61M 31/00*     (2006.01)
*A61K 39/145*    (2006.01)
(Continued)

(52) U.S. Cl.
CPC .............. *A61K 39/145* (2013.01); *A61B 17/205* (2013.01); *A61K 2039/541* (2013.01);
(Continued)

(58) Field of Classification Search
CPC ........... A61B 17/205; A61K 2039/541; A61K 2039/545; A61K 39/145; A61M 2037/0046; A61M 2037/0061; A61M 37/0015; C12N 2760/16134; C12N 2760/16234
USPC ...................... 604/173, 506; 424/184.1, 206.1
See application file for complete search history.

(56) References Cited

U.S. PATENT DOCUMENTS 4,659,569 A * 4/1987 Mitsuhashi et al. ........ 424/194.1
5,456,914 A * 10/1995 Stine et al. .................. 424/256.1
(Continued)

FOREIGN PATENT DOCUMENTS

JP    2006-341089 A    12/2006
JP    2007-37626 A    2/2007
(Continued)

OTHER PUBLICATIONS

Harvinder S. Gill, et al.; "Coating Formulations for Microneedles"; Pharmaceutical Research; vol. 24; No. 7; Jul. 2007; pp. 1369-1380.
(Continued)

*Primary Examiner* — Kami A Bosworth
*Assistant Examiner* — Imani Hayman
(74) *Attorney, Agent, or Firm* — Sughrue Mion, PLLC

(57) ABSTRACT

The present invention provides a method for enhancing the immunogenicity using a microneedle device capable of enhancing the immunogenicity of an influenza vaccine. According to the method for enhancing the immunogenicity using the present microneedle device, a microneedle device having microneedles made of polylactic acid, coated with an influenza vaccine composed of an antigen having type A strain (H1N1), type A strain (H3N2), and type B strain as active ingredients is brought into direct contact with the skin so as to transcutaneously administer the aforementioned influenza vaccine. After the transcutaneous administration, lauryl alcohol is applied to the site of the skin where the microneedle device has been brought into direct contact.

9 Claims, 4 Drawing Sheets

(51) Int. Cl.
*A61B 17/20* (2006.01)
*A61M 37/00* (2006.01)
*A61K 39/00* (2006.01)

(52) U.S. Cl.
CPC ...... *A61K2039/545* (2013.01); *A61M 37/0015* (2013.01); *A61M 2037/0046* (2013.01); *A61M 2037/0061* (2013.01); *C12N 2760/16134* (2013.01); *C12N 2760/16234* (2013.01)

(56) References Cited

U.S. PATENT DOCUMENTS

| | | | |
|---|---|---|---|
| 7,914,813 | B2 | 3/2011 | Adachi et al. |
| 2002/0082543 | A1* | 6/2002 | Park et al. ........................ 604/21 |
| 2004/0109869 | A1 | 6/2004 | Glenn et al. |
| 2005/0220854 | A1 | 10/2005 | Maa et al. |
| 2006/0163215 | A1 | 7/2006 | Maenosono et al. |
| 2007/0250018 | A1 | 10/2007 | Adachi et al. |
| 2008/0262444 | A1 | 10/2008 | Takada |
| 2009/0099502 | A1 | 4/2009 | Tokumoto et al. |
| 2011/0081418 | A1* | 4/2011 | Yamaguchi et al. .......... 424/490 |

FOREIGN PATENT DOCUMENTS

| | | |
|---|---|---|
| JP | 2007-530680 A | 11/2007 |
| JP | 2008-74763 A | 4/2008 |
| WO | 0207813 A1 | 1/2002 |
| WO | 2005044366 A2 | 5/2005 |
| WO | 2006075689 A1 | 7/2006 |
| WO | 2006075716 A1 | 7/2006 |
| WO | 2006/080508 A1 | 8/2006 |
| WO | 2006121110 A1 | 11/2006 |
| WO | 2007/015441 A1 | 2/2007 |
| WO | 2007012114 A1 | 2/2007 |
| WO | 2007/116959 A1 | 10/2007 |
| WO | 2009/051147 A1 | 4/2009 |

OTHER PUBLICATIONS

Chisato Yoshimura, et al., "Polylactic Acid-sei Microneedle Array no Kino Hyoka", Abstracts of Annual Meeting of Pharmaceutical Society of Japan, 2004, p. 68, No. 124th, No. 4, III-173.

James A. Matriano, et al., "Macroflux Microprojection Array Patch Technology: a New and Efficient Approach for Intracutaneous Immunization", Pharmaceutical Research, Jan. 2002, pp. 63-70, vol. 19, No. 1.

* cited by examiner

NASAL CAVITY

LUNG

HI ANTIBODY TITER AGAINST HA ANTIGEN (A/SOLOMON)
(AT THE TIME OF TERMINATION OF EXPERIMENT)

*HI ANTIBODY TITERS EXCEED 640 (3 CASES IN SC-3 μg, 1 CASE IN MN-3 μg) ARE SHOWN AS 1280.

MICRONEEDLE DEVICE, AND METHOD FOR ENHANCING THE EFFICACY OF INFLUENZA VACCINE BY USING MICRONEEDLE DEVICE

TECHNICAL FIELD

The present invention relates to a method for enhancing the immunogenicity using a microneedle device.

BACKGROUND ART

The skin consists of the outermost stratum corneum, epidermis, dermis, and subcutaneous connective tissues. Normally, the stratum corneum, which consists of layers of dead cells and lipid bilayers, exhibits a strong barrier function against numerous substances. Antigen-presenting cells called Langerhans cells are present in the dermal layer and serve immunological functions. Langerhans cells capture protein antigens invaded into the skin, degrade them within the cells, and display peptide fragments on the MHC molecules. MHC-peptide complexes migrate from the afferent lymph vessel to the subcortical layer of the regional lymph node, where they come into contact with T-cells via interdigitating cells. As Langerhans cells migrate in this way, antigens are conveyed to $T_H$ cells residing in the lymph node. Langerhans cells have MHC class II molecules, which are necessary for presenting antigens to $T_H$ cells.

Although vaccine administration into the dermis is known to be effective, owing to the strong barrier function of the stratum corneum of the skin as described above, there is a problem of accuracy associated with administration into the dermis that has limited thickness of 300 to 2000 μm using an injection needle due to technical difficulty.

As means for solving the above problem, microneedles have been developed. Microneedles of various sizes and shapes (extremely small projections having a height of approximately several tens to several hundreds micrometers) have been developed for the purpose of puncturing the outermost stratum corneum, which are anticipated to serve particularly as a method of noninvasive vaccine administration.

Also, various methods of drug application using a device with microneedles have been developed. For example, a method of administering a drug coated on the surface of microneedles, a method of forming a hole (a hollow needle) or a groove on a needle to allow a drug or a biological component to penetrate therethrough, and a method of incorporating a drug into a needle itself are proposed. In the light of the fact that all of these microneedle devices are equipped with extremely small projections having a height of approximately several tens to several hundreds micrometers (microneedles), transcutaneous absorbability and absorption efficiency of a drug are considered to be greatly varied depending on the method of drug application.

For example, as a method for efficiently promoting the transcutaneous absorbability of antigens (vaccines) using a microneedle, a method of coating a part of the microneedle surface with a drug is disclosed in, for example, Non Patent Literature 1. It indicates that when a part of a microneedle (particularly, only the needle part) is coated with antigens (vaccines), all or nearly all of the applied antigens (vaccines) are delivered into the body, hence the above method is useful as means for accurate intradermal administration.

Meanwhile, recently, the importance of efficient and safe administration of medicinal substances such as a diagnostic agent and a drug has been recognized. Particularly these days, as a countermeasure for a new strain of the influenza virus, development of a prepandemic vaccine (A/H5N1 subtype) is in progress (Non Patent Literature 2). In a vaccination method of this vaccine, subcutaneous or intramuscular vaccination has to be given twice, three weeks apart. In consideration of the pandemic of this type of new strain of the influenza virus, induction of immunity in as many people as possible with as little vaccine as possible becomes a challenge. For this, development of an efficient and simple method of vaccine administration is demanded.

Further, the "influenza HA vaccine", which satisfies the minimum requirements for biological products as provided in the Japanese Pharmacopoeia, is widely used as an influenza vaccine at present in Japan. It is a trivalent vaccine containing type A (H1N1), type A (H3N2), and type B. As the dosing regimen, the vaccine has to be given by a subcutaneous injection once, or twice, one to four weeks apart. It is known that, in the rare occasion, there are still some people in whom the immunity is not easily induced. For this reason also, efficient vaccine administration is necessary.

A microneedle preparation using an influenza vaccine is disclosed in Patent Literature 1. While the disclosure regarding the microneedle preparation includes the administration method and the formulation of the influenza vaccine, a relationship between the dose of antigens administered by microneedles and the effect (antibody titer) is not examined at a dose equal to or less than that administered using an intramuscular injection (IM) or a subcutaneous injection (Sc). Further, no measures for reducing the dose of antigens and enhancing the effect are discussed.

Patent Literature 2 discloses a method of transcutaneous immunostimulation in which, after an influenza vaccine is administered orally, intranasally, by an injection, an adjuvant is applied to the skin surface. Although the above document exemplifies the administration methods involving oral, skeletal muscular, and subcutaneous routes, etc., it does not describe the administration using microneedles.

Patent Literature 3 discloses the administration using hollow microneedles with an aim to reduce the amount of therapeutic substances while achieving the therapeutic effect; however, there is no description relating to the induction of the immunity.

CITATION LIST

Patent Literature

Patent Literature 1: National Publication of International Patent Application No. 2007-530680
Patent Literature 2: National Publication of International Patent Application No. 2004-529906
Patent Literature 3: National Publication of International Patent Application No. 2006-506103

Non Patent Literature

Non Patent Literature 1: Pharma. Res. 19(1), 63-70 (2002)
Non Patent Literature 2: Japanese Society for Vaccinology, Newsletter, Vol. 12 (Jan. 10, 2007)

SUMMARY OF INVENTION

Technical Problem

In spite of the possibility that coating microneedles with an influenza vaccine and administering the influenza vaccine accurately into the dermis would enable efficient and simple vaccine administration, as described above, the comparison between the administration of influenza vaccine by microneedles and that by an injection have not been sufficiently conducted.

An object of the present invention is to provide a method for enhancing the immunogenicity using a microneedle device capable of enhancing the immunogenicity of an influenza vaccine.

Solution to Problem

Under the above-described background art, the present inventors continued their research day after day, and as a result, have found that transcutaneous administration of an influenza vaccine using microneedles coated with an influenza vaccine composed of an antigen having type A strain (H1N1), type A strain (H3N2), and type B strain as active ingredients can increase the antibody property of the influenza vaccine compared with a subcutaneous injection. Further, efficient and marked increases in the antibody titer against the subtypes of all three strains were confirmed with application of lauryl alcohol to the site where the microneedles coated with an influenza vaccine have been transcutaneously administered, in comparison with subcutaneous administration.

That is, according to the method for enhancing the immunogenicity using a microneedle device of the present invention, a microneedle device having microneedles made of polylactic acid and coated with an influenza vaccine composed of an antigen having type A strain (H1N1), type A strain (H3N2), and type B strain as active ingredients is brought into direct contact with the skin so as to transcutaneously administer the influenza vaccine. At this point, after the transcutaneous administration of the influenza vaccine, the immunogenicity is further enhanced by applying lauryl alcohol having an adjuvant effect to the site of the skin where the microneedle device has been brought into direct contact. An immunogenicity-enhancing effect is anticipated also with application of other skin-permeable substances having an adjuvant activity.

The microneedle device of the present invention has microneedles made of polylactic acid and coated with an influenza vaccine composed of an antigen having type A strain (H1N1), type A strain (H3N2), and type B strain as active ingredients. At this point, the aforementioned coating preferably contains pullulan as a coating carrier. Also, the aforementioned coating can contain lauryl alcohol.

Advantageous Effects of Invention

According to the present invention, the immunogenicity of the subtypes of all three strains of an influenza vaccine composed of an antigen having type A strain (H1N1), type A strain (H3N2), and type B strain as active ingredients can be increased by efficient and simple operations compared with subcutaneous administration by an injection. Use of a microneedle device for transcutaneous immunostimulation stimulates an influenza vaccine-induced immune response, whereby reducing the effective dose of antigens in the vaccine.

DESCRIPTION OF EMBODIMENTS

Figure 1:
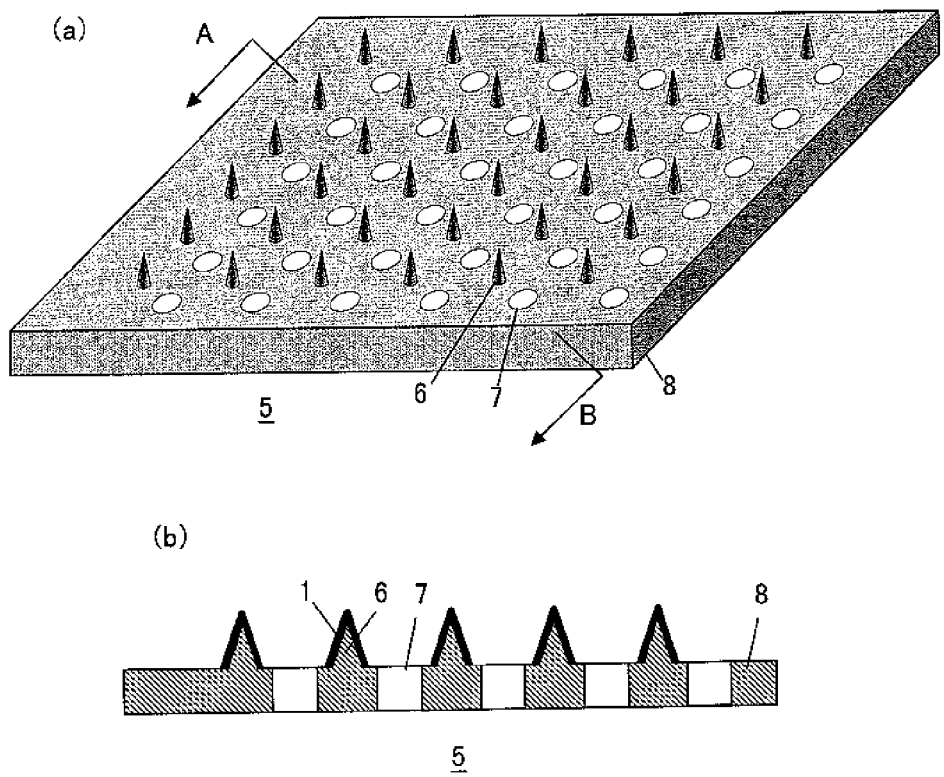
FIG. 1 is a diagram illustrating an example of the microneedle device of the present invention, in which (a) is an oblique perspective view and (b) is a cross-sectional view taken along A-B of (a).

FIG. 1 is a diagram illustrating an example of the microneedle devices of the present invention, in which (a) is an oblique perspective view and (b) is a cross-sectional view taken along A-B of (a). As shown in FIG. 1 (*a*), a microneedle device of the present invention (interface) 5 has a microneedle base 8 and a plurality of microneedles 6 arranged two-dimensionally so that the microneedles are capable of puncturing the skin or the mucus. The microneedle base 8 has a plurality of openings 7 arranged in such a manner that each of the openings 7 corresponds to each of the microneedles 6. While the microneedle 6 is in a conical shape in the present example, the present invention is not limited thereto and may also be in a polygonal pyramid shape such as a square pyramid or in other shapes. Further, although the plurality of microneedles 6 and the plurality of openings 7 are each alternately arranged in a square lattice pattern, the present invention is not limited thereto. Furthermore, although the number of the microneedles 6 and that of the openings 7 are 1:1 in the figure, the present invention is not limited thereto. The present invention also encompasses those that do not contain the opening 7.

In the present example, a coating of an influenza vaccine composed of an antigen having type A strain (H1N1), type A strain (H3N2), and type B strain as active ingredients is provided on a part or the entire surface of the microneedle 6. For example, as shown in FIG. 1 (*b*), the coating 1 is applied to the surface of each microneedle 6. While the coating 1 is applied to the entire microneedle 6, it can be applied to a part thereof. At the time of application, the microneedle base surface onto which the microneedles 6 are arranged as shown in FIG. 1 (*a*) is brought into direct contact with the skin. Then, as a medicine-dissolved solution is poured from the reverse side, a liquid flows out from each opening 7 and reaches each microneedle 6, whereby the aforementioned influenza vaccine is transcutaneously absorbed. At this point, the opening 7 is not essential, and the liquid may be supplied to the microneedle 6 by different means without using the opening 7. Also, the coating 1 can be dissolved, without the external liquid supply, in the body fluid encountered at the time of skin puncture by the microneedle, whereby the influenza vaccine can be released inside the skin.

A microneedle in the microneedle device is composed of a microneedle (needle) for puncturing the skin or the mucus supported with a base, and the microneedles are arranged on the base. The microneedle has a minute structure, and the height (length) of the microneedle h is preferably 50 μm to 700 μm, more preferably 100 μm to 600 μm, and even more preferably 200 μm to 500 μm. At this point, the length of the microneedle is set at 50 μm or more so as to ensure transcutaneous influenza vaccine administration, while the length of the microneedle is set at 700 μm or less so as to avoid the contact between the microneedle and nerves to certainly reduce the possibility of pain, and simultaneously to certainly avoid the possibility of bleeding. Also, when the length of the microneedle is 700 μm or less, the amount of influenza vaccine to be released inside the skin can be efficiently administered.

At this point, microneedle refers to a projecting structure including, in a broad sense, a needle shape or a structure containing a needle shape. When it is in a conical shape, the diameter of the basal surface thereof is normally approximately 50 to 200 μm. Also, the microneedle is not limited to a structure having a needle shape with a sharp tip but include a structure without a sharp tip. The microneedle is preferably produced with non-metallic, synthetic or natural resin materials. Also, while the microneedle is in a conical shape in the present example, the present invention is not limited thereto and may be in a polygonal pyramid shape such as a square pyramid, or in other shapes.

The microneedle base is a foundation for supporting the microneedle, and no limitation is imposed on its form. For example, as shown in FIG. 1, the base may be one with a through hole (opening). In that case, in addition to that an influenza vaccine-dissolving solution can be poured from the reverse side of the base to dissolve the influenza vaccine coated on the microneedle, the influenza vaccine can be administered by flowing through via the opening and the microneedle. Examples of a material of the microneedle or the base include silicon, silicon dioxide, ceramics, metals (such as stainless steel, titanium, nickel, molybdenum, chromium, and cobalt) and synthetic or natural resin materials. However, in consideration of the antigenicity of the microneedle and the unit price of a material, a biodegradable polymer such as polylactic acid, polyglycolide, polylactic acid-CO-polyglycolide, pullulan, capronolactone, polyurethane, and polyanhydride, and a synthetic or natural resin material such as polycarbonate, polymethacrylic acid, ethylenevinyl acetate, polytetrafluoroethylene, polyoxymethylene, which are non-biodegradable polymers, are particularly preferable. Further, polysaccharide such as hyaluronic acid, pullulan, dextran, dextrin, or chondroitin sulfate is also suitable. Particularly, polylactic acid is a biodegradable resin and has been practically utilized in an implant preparation (National Publication of International Application No. 2002-517300 or Journal of Controlled Release 104 (2005) 51-66); therefore, it is one of the most suitable materials of the microneedle from the viewpoints of strength and safety.

As to the density of microneedles (needles), the microneedles are typically arranged in rows and spaced apart from each other so that a density of approximately one to 10 needles per millimeter (mm) is provided. Generally, rows are spaced apart from each other by a distance substantially equal to the space between the needles in a row. The needle density is 100 to 10000 needles, preferably 100 to 5000 needles, more preferably 200 to 2000 needles, even more preferably 400 to 1000 needles, per $cm^2$. A needle density of 100 or more needles enables efficient puncture of the skin, while a needle density of more than 10000 needles makes it difficult to impart strength capable of puncturing the skin to the microneedles.

Examples of a production method of the microneedle include wet etching process or dry etching process using a silicon base, precision machining using metals or resins (such as electric discharge method, laser processing, dicing processing, hot embossing, and injection mold processing), and machinery cutting. The needle part and the support part are molded into an integrated unit by these processing methods. Exemplary methods for hollowing the needle part include a method in which, following the production of the needle part, a secondary processing such as laser processing is carried out.

In the process of coating the microneedle, in order to minimize the changes in drug concentration and physical properties caused by volatilization of solvent contained in a coating liquid, temperature and humidity in the installation environment of an apparatus can be controlled at constant levels. In order to prevent solvent evaporation, it is preferable to either decrease the temperature or raise the humidity, or control both of them. The humidity at room temperature when the temperature is not controlled is 50 to 100% RH, preferably 70.0 to 100% RH, as relative humidity. A relative humidity of 50% RH or less may cause solvent evaporation, possibly causing the changes in physical properties of the coating liquid. While no particular limitation is imposed on the humidification method as long as the intended humidity condition is attained, examples thereof include gas system, steam vapor system, and water spray system.

The influenza vaccine is not limited by the type of viral strain. The influenza vaccine may range from a seasonal vaccine to a pandemic vaccine, and in the case of a pandemic vaccine, it may contain type A, type B, type C, and subtypes existing for each of them. For example, the "influenza HA vaccine" satisfying the minimum requirements for biological products as provided in the Japanese Pharmacopoeia is an influenza vaccine composed of an antigen having type A strain (H1N1), type A strain (H3N2), and type B strain as active ingredients.

The coating liquid used for coating the microneedle may contain, in addition to the influenza vaccine, a coating carrier and a liquid composition. Also, the coating of the present invention is preferably in a state in which the coating liquid stays and is fixed onto the microneedle (needle), and in order to achieve this state, a drying process may be additionally performed for fixation of the coating liquid.

The coating carrier is preferably a polysaccharide carrier that is relatively compatible (having a property of being homogeneously mixed) with the influenza vaccine. The coating carrier is preferably polyhydroxymethylcellulose, hydroxypropylcellulose, polyhydroxypropylmethylcellulose, polymethylcellulose, dextran, polyethylene glycol, pullulan, carmellose sodium, chondroitin sulfate, hyaluronic acid, dextran, gum arabic, and the like, and further, more preferably hydroxypropylcellulose, pullulan, and gum arabic. Further, the coating carrier is even more preferably hydroxypropylcellulose (HPC-SSL (molecular weight: 15,000 to 30,000), HPC-SL (molecular weight: 30,000 to 50,000), HPC-L (molecular weight: 55,000 to 70,000), HPC-M (molecular weight: 110,000 to 150,000), and HPC-H (molecular weight: 250,000 to 400,000)), pullulan, and hyaluronic acid. Particularly, pullulan is most preferable from the aspect of the compatibility with the influenza vaccine.

The content of coating carrier in the entire coating liquid is 1 to 70% by weight, preferably 1 to 40% by weight, and particularly preferably 3 to 25% by weight. Also, the coating carrier may have to have a certain degree of viscosity to prevent it from dripping, and a viscosity of approximately 100 to 100000 cps is necessary. More preferably, the viscosity is 500 to 60000 cps. When the viscosity is within the above range, the desired amount of coating liquid can be applied at once irrespective of the material of the microneedle. Also, there is a general tendency that the higher the viscosity, the larger the amount of coating liquid.

The liquid composition to be used for coating the microneedle is prepared by mixing a biocompatible carrier, the influenza vaccine to be delivered, and in some cases, any of coating aids with a volatile liquid. The volatile liquid can be water, dimethyl sulfoxide, dimethyl formamide, ethanol, isopropyl alcohol, a mixture thereof, and the like. Among them, water is most preferable. A coating liquid in a liquid state or a suspension typically can have an influenza vaccine concentration of 0.1 to 65% by weight, preferably 1 to 30% by weight, more preferably 3 to 20% by weight.

Other known pharmaceutical aids may be added to the coating as long as they do not adversely affect characteristics of necessary solubility and viscosity of the coating as well as nature and physical properties of the dried coating.

The thickness of coating of the microneedle is less than 50 μm, preferably less than 25 μm, and more preferably 1 to 10 μm. Generally, the thickness of coating is an average thickness as measured over the surface of the dried microneedle. The thickness of coating can generally be increased by application of multiple films of coating carriers, namely, by repeating a coating process after fixation of the coating carrier.

As described above, the height (length) of the microneedle h is preferably 50 μm to 700 μm. Although the height of the coating of the microneedle H varies depending on the height of the microneedle h, H can be in a range of 0 μm to 700 normally in a range of 10 μm to 700 μm, and preferably approximately 30 μm to 500 μm.

In order to make the induction of the immunity by the influenza vaccine using the microneedle device of the present invention more perfect, for example aliphatic alcohols having an adjuvant effect can be applied to the site where the influenza vaccine has been administered by the microneedle device of the present invention. As such aliphatic alcohols, linear or branched aliphatic alcohols are preferable. While no particular limitation is imposed on the carbon number and the molecular weight of such aliphatic alcohols, in consideration of the skin permeability, the carbon number is more preferably 8 to 20. Further, these aliphatic alcohols may be either saturated or unsaturated.

While many of these aliphatic alcohols are utilized as an absorption promoter in transcutaneous absorption, the aliphatic alcohols according to the present invention can be anticipated to have an adjuvant effect in addition to an absorption-promoting action in reference to WO 2007/015441.

Examples of such aliphatic alcohols include octyldodecanol, lauryl alcohol, oleyl alcohol, isostearyl alcohol, and decanol. Among them, lauryl alcohol, octyldodecanol, and isostearyl alcohol are particularly preferable, among which lauryl alcohol is most preferable.

When the aliphatic alcohols of the present invention are mixed in a vaccine, they are mixed preferably in an amount of 0.1 to 99% by weight, more preferably in an amount of 5 to 90% by weight, and particularly preferably in an amount of 10 to 80% by weight. The content of the aliphatic alcohols in the most preferable composition is 15 to 75% by weight.

Also, when applying the aliphatic alcohols following vaccine administration, while of course they can be applied alone, they can also contain a known pharmaceutical aid. As to the composition of the above substances, they can be preferably mixed at 0.1 to 99% by weight, more preferably 5 to 90% by weight, and particularly preferably 10 to 80% by weight. The content of the aliphatic alcohols in the most preferable composition is 15 to 75% by weight.

While the administration time of the microneedle device of the present invention is considered to be approximately 4 minutes to 600 minutes, it is preferable to keep it as short as possible for improving compliance.

The most suitable administration time is observed at the time when administration of most of the influenza vaccine coated on the microneedle device is completed, which is considered to be varied depending on the composition of the coating and the adjuvant as well as the shape of the microneedle.

Preferable administration time of the microneedle device is 4 minutes to 180 minutes. When it is shorter than 4 minutes, the administration of the influenza vaccine may be insufficient because it takes time to dissolve. An administration time of longer than 180 minutes is not preferable in terms of compliance. Further, the administration time is preferably 4 minutes to 60 minutes, and most preferably 4 minutes to 10 minutes.

The microneedle device of the present invention stimulates an immune response in the skin, whereby increasing the serum IgG antibody titer. Further, it can also increase the IgA antibody titer without requiring addition of an adjuvant. Particularly, the IgA antibody titer is locally increased, for example in the lungs and nasal mucus.

EXAMPLES

Experimental Example 1

An influenza HA vaccine containing an antigen having type A strain (H1N1), type A strain (H3N2), and type B strain as active ingredients that was prepared as described below was concentrated by centrifugation using BIOMAX-10K (manufactured by Millipore). The influenza HA vaccine thus concentrated was mixed with a high molecular weight polymer (pullulan) and coated on microneedles made of polylactic acid (a height of approximately 300 μm, a density of 841 needles/cm$^2$, in a square pyramid shape) while maintaining a relative humidity of 90 to 100% RH by a humidifier. The content of each antigen in the coating was 0.3 μg/patch. The abdominal hair of four-week-old ddY mice (female) was shaven, and the mice were administered with the coated microneedles for two hours via skin puncture under anesthesia. After the vaccine was partially administered, an adjuvant liquid (lauryl alcohol) was applied dropwise to the administration site, and then the mice were similarly administered for two hours via skin puncture. The mice in a subcutaneous administration group were subcutaneously administered in the back in an amount of 1 μg/50 μL/head. After one week, the mice were given booster vaccination under the same conditions, and one week after that, the blood was drawn and the antibody titers against the above three types of strains were measured. Likewise, the aforementioned vaccine was subcutaneously administered by an injection in an amount three times as much as the amount coated on the aforementioned microneedles, and the antibody titers were measured. The results thus obtained are shown in Table 1.

(Preparation of Influenza Virus HA Antigen)

Fertile eggs (fertilized eggs) were kept warm at 38 to 39° C. for approximately 11 days in an incubator, in which development of embryos was confirmed. Then, a hole just enough for an injection needle to pass through was made in the egg shell, from which influenza viruses (A/Hiroshima (H3N2), A/New Caledonia (H1N1), and B/Malaysia), which were the strains used for vaccine production, were directly injected into allantoic fluid. Then, the hole was sealed and the eggs were returned to the incubator and kept warm at 32 to 36° C. for three days or so. Subsequently, virus-inoculated eggs were refrigerated overnight and the egg shell was cut off, and allantoic fluids were aseptically collected. After removing impurities such as blood from the fluids thus collected, virus particles were purified and concentrated by sucrose density gradient centrifugation using a zonal centrifuge rotor. The suspensions of the influenza virus thus obtained were treated with ether, to which formalin was then added.

The amounts of the influenza HA antigens of the three strains prepared as above were measured in accordance with the single radial immunodiffusion test provided as the potency tests under Influenza HA Vaccine in the minimum requirements for biological products (Ministry of Health, Labour and Welfare). The influenza HA antigens were then mixed and diluted, thereby the influenza HA vaccine was provided.

(Measurement of the HI Antibody Titer)

The HI antibody titer in mouse serum was measured separately for each of the three strains of the HA antigens (type A strain (H1N1), type A strain (H3N2), and type B strain) in accordance with the method shown below.

Firstly, 100 µL of mouse serum were subjected to pretreatment to eliminate a non-specific erythrocyte inhibitory activity and a spontaneous agglutination factor of erythrocyte. Subsequently, the pretreated mouse serum was diluted 10-fold, and on a microplate, further subjected to 2-fold serial dilution (25 µL/well) from 10-fold to 640-fold using PBS. To the resulting diluted serum solutions an HA antigen liquid (influenza HI reagent "Seiken", Denka Seiken Co., Ltd.) that had been adjusted to have a 4-fold erythrocyte agglutination activity in advance was added in an equal amount (25 µL/well). After shaking well in a mixer, the plate was left to stand at room temperature for one hour, and a 0.5% chicken erythrocyte suspension was added in an amount of 50 µL/well. After leaving the plate to stand at room temperature for one hour, a maximum dilution factor at which erythrocyte agglutination was inhibited was measured, which was provided as the H1 antibody titer.

TABLE 1

| Means of administration | Animal No. | HI antibody titer | | |
|---|---|---|---|---|
| | | A (H1N1) | A (H3N2) | B |
| Microneedle | 1 | 40 | 40 | 10 |
| | 2 | 40 | 10 | 10 |
| | 3 | 20 | 20 | <10 |
| | 4 | 10 | 10 | <10 |
| | 5 | 10 | 10 | <10 |
| Microneedle (lauryl alcohol) | 1 | 160 | 160 | 40 |
| | 2 | 40 | 20 | 160 |
| | 3 | 40 | 80 | 20 |
| | 4 | 40 | 80 | 20 |
| | 5 | 40 | 40 | 20 |
| Subcutaneous administration | 1 | 10 | 10 | 10 |
| | 2 | 10 | 10 | <10 |
| | 3 | 10 | 10 | 20 |
| | 4 | 40 | 20 | 10 |
| | 5 | <10 | 10 | 20 |
| | 6 | 10 | 10 | <10 |

As shown in Table 1, it was revealed that, with use of a microneedle device of the present invention, an effect nearly equivalent to subcutaneous administration was exhibited at one-third of the amount of antigen administered by subcutaneous administration. Based on the above results it was confirmed that an efficient increase in the HI antibody titer of approximately three times as much as that observed with subcutaneous administration by an injection was achieved with administration using a microneedle device of the present invention.

Further, it was revealed that, when lauryl alcohol was used as an adjuvant in combination, not only was the HI antibody titer for type A increased but also a remarkable effect was exerted on type B, for which the HI antibody titer had been known not to be increased easily (refer to Influenza HA Vaccine in Biological products in Japanese Pharmacopoeia).

Experimental Example 2

An influenza HA vaccine containing an antigen having type A strain (H1N1) as an active ingredient that was prepared as described below was concentrated by centrifugation using BIOMAX-10K (manufactured by Millipore). The influenza HA vaccine thus concentrated was mixed with a high molecular weight polymer (pullulan), and the resulting mixture was coated on microneedles made of polylactic acid (a height of approximately 300 µm, a density of 841 needles/cm², in a square pyramid shape) under the condition of a relative humidity of 90 to 100% RH in a content of 0.3 µg/patch.

The abdominal hair of 10-week-old ddY mice (female) was shaven, and the mice in the microneedle administration group were administered with the aforementioned microneedles for two hours via skin puncture under anesthesia. After one week, and after another week, the mice were given booster vaccination for a total of two times under the same conditions, and another two weeks after that, the blood was drawn and nasal and lung lavages were performed.

Meanwhile, the mice in the subcutaneous administration group were subcutaneously administered with the influenza HA vaccine/PBS in the back in an amount of 3 µg/50 µL/head. After one week, and after another week, the mice were given booster vaccination for a total of two times under the same conditions, and another two weeks after that, the blood was drawn.

The IgG antibody titer in the serum obtained as described above was measured in accordance with the method described below, and the IgA antibody titer in lavage fluids obtained by the nasal and lung lavages was measured in accordance with the method described below (n=4).

Experimental Example 3

An influenza HA vaccine containing an antigen having type A strain (H1N1) as an active ingredient that was prepared as described below was concentrated by centrifugation using BIOMAX-10K (manufactured by Millipore). The influenza HA vaccine thus concentrated was mixed with a high molecular weight polymer (pullulan), and the resulting mixture was coated on microneedles made of polylactic acid (a height of approximately 300 µm, a density of 841 needles/cm², in a square pyramid shape) under the condition of a relative humidity of 90 to 100% RH in a content of 0.3 µg/patch.

The antigen was extracted from unused microneedles, and protein was quantitated and then calculated in terms of HA. As a result, the following values were obtained; first time administration: 2.5 µg, second time: 1.5 µg, and third time: 3.9 µg. Thus, equal amounts of antigens were administered to the mice in a subcutaneous administration group.

Administration to the animals was performed as follows; the abdominal hair of the mice (ddy/female/4 W) was shaven day before administration. On the day of administration, the site of puncture was sterilized with alcohol-soaked cotton under nembutal anesthesia, and the microneedles were pressed with finger for 5 seconds, and then the mice were taped around for five or 120 minutes to fix the microneedles. <Group compositions: (1) subcutaneous administration (four mice), (2) microneedle administration for five minutes (five mice), and (3) microneedle administration for 120 minutes (five mice)>

Administration schedule was as follows; administration was performed for a total of three times, namely the initial administration, two weeks after the initial administration, and four weeks after the initial administration. Blood was drawn after two weeks, four weeks, and five weeks (2 w, 4 w, and 5 w). After blood drawing, the influenza antigen-specific antibody titer (IgG) was measured by ELISA. Also, the HI antibody titer in the serum after five weeks (5 w) was measured.

Figure 5:
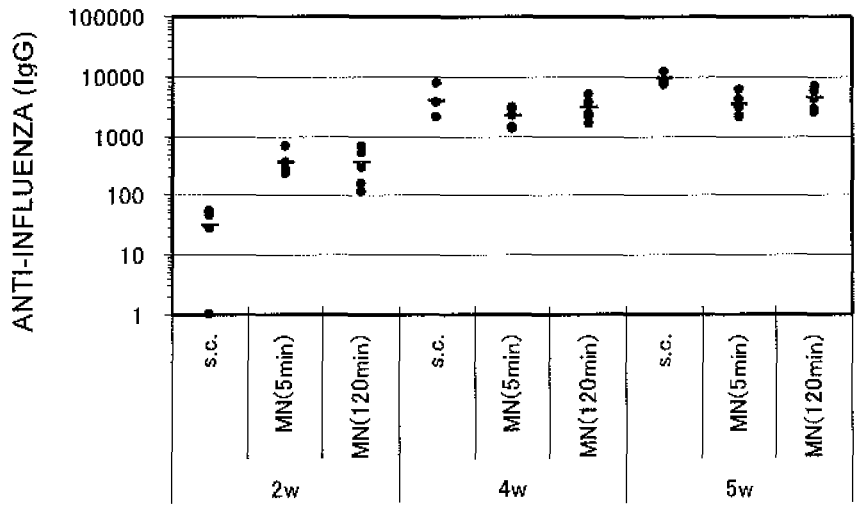
FIG. 5 is a graph showing an example of the measurement results of individual antibody titers over time after influenza vaccine administration.
Figure 6:
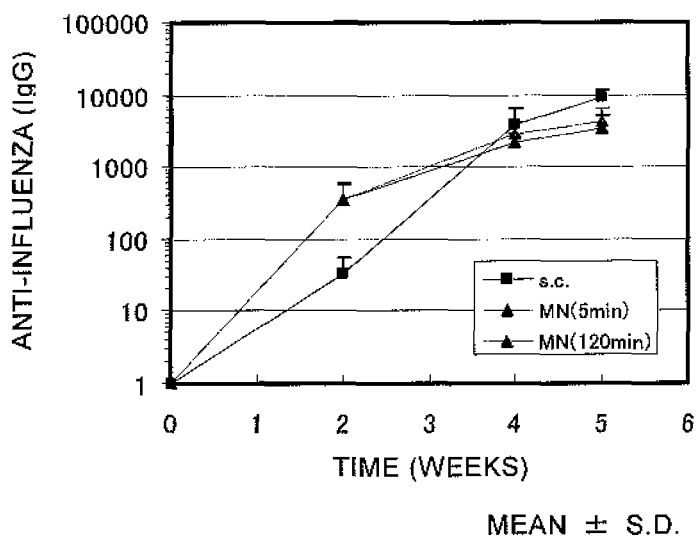
FIG. 6 is a graph showing an example of the changes in the antibody titer after influenza vaccine administration.

FIG. 5 is a graph showing an example of the measurement results of individual antibody titers over time after influenza vaccine administration. FIG. 6 is a graph showing an example of the changes in the antibody titer after influenza vaccine administration. As shown in FIGS. 5 and 6, there was no big difference in the IgG antibody titer between the mice given the administration of the microneedles (MN) via puncture for five minutes and for 120 minutes. Further, the effect was almost equivalent to that of subcutaneous administration (s.c.) Further, as shown in Table 2, the HI antibody titer was also nearly equal between the mice given the administration of the microneedles (MN) via puncture for five minutes and for 120 minutes, and the effect was at the same level as that achieved in a subcutaneous administration (s.c.) group. Thus, it is considered that a sufficient HI antibody titer production can be anticipated with administration via puncture for five minutes.

TABLE 2

Individual HI antibody titers at the final blood drawing

| Animal No. | s.c. | MN (5 min) | MN (120 min) |
|---|---|---|---|
| 1 | 320 | n.d.* | 160 |
| 2 | n.d.* | 320 | 320 |
| 3 | 320 | 320 | 320 |
| 4 | 640< | 320 | 320 |
| 5 |  | 160 | 160 | n.d.*: Non-detectable due to insufficient serum (Measurement of the IgG Antibody Titer)

Serum was separated from the blood drawn and then inactivated (treatment at 56° C. for 30 minutes), which was used as a sample. A virus antigen was diluted with a coating buffer at 0.2 µg/mL and added to wells in an amount of 100 µL/well, and left to stand at 4° C. overnight. The immobilized plate thus obtained was washed with 300 µL/well of wash buffer three times, after which a blocking buffer was added in an amount of 300 µL/well. Reactions were allowed to proceed at 37° C. for 15 minutes. Thereafter, the plate was washed with 300 µL/well of wash buffer three times. Meanwhile, the sample was diluted 100-fold with a dilution butter, followed by 2-fold serial dilutions. The samples thus prepared were added to each well in an amount of 100 µL/well, and reactions were allowed to proceed at 37° C. for one hour.

Subsequently, the plate was washed with 300 µL/well of wash buffer three times, to which a diluted HRP-labeled anti-mouse IgG antibody was added in an amount of 100 µL/well, and the reaction was allowed to proceed at 37° C. for one hour. Then, the plate was washed with 300 µL/well of buffer three times, after which a solution of ABTS peroxidase substrate was added in an amount of 100 µL/well. The reaction was allowed to proceed in the dark at room temperature for 30 minutes, after which a peroxidase stop solution was added in an amount of 100 µL/well to terminate the reaction. Absorbance at 405 nm was then measured.
Coating buffer; 0.05M carbonate buffer (pH 9.5)
Wash buffer; 0.05% Tween20-containing PBS (PBS-T)
Blocking buffer; 1% BSA-containing PBS
Dilution buffer; 1% BSA-containing PBS-T (Measurement of the IgA Antibody Titer)

Nasal lavage fluid and lung lavage fluid are used as samples. A virus antigen was diluted with a coating buffer at 0.1 µg/mL and added to wells in an amount of 100 µL/well, and left to stand at 4° C. overnight. The immobilized plate thus obtained was washed with 300 µL/well of wash buffer three times, after which a blocking buffer was added in an amount of 300 µL/well. The reaction was allowed to proceed at 37° C. for 15 minutes. Thereafter, the plate was washed with 300 µL/well of wash buffer three times, and the samples were diluted 2-fold with a dilution buffer. The samples thus prepared were added to each well in an amount of 100 µL/well, and the reaction was allowed to proceed at 37° C. for one hour.

Figure 2:
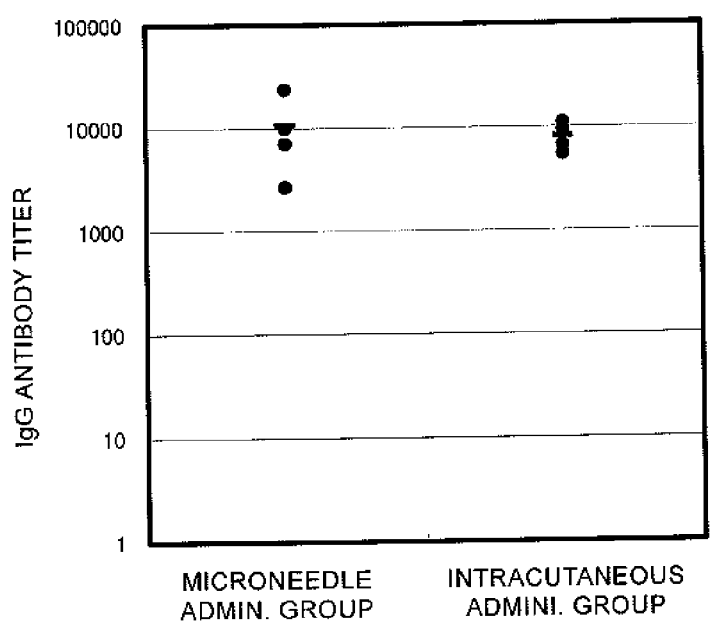
FIG. 2 is a graph showing a comparison between a microneedle administration group and a subcutaneous administration group for the IgG antibody titer.
Figure 3:
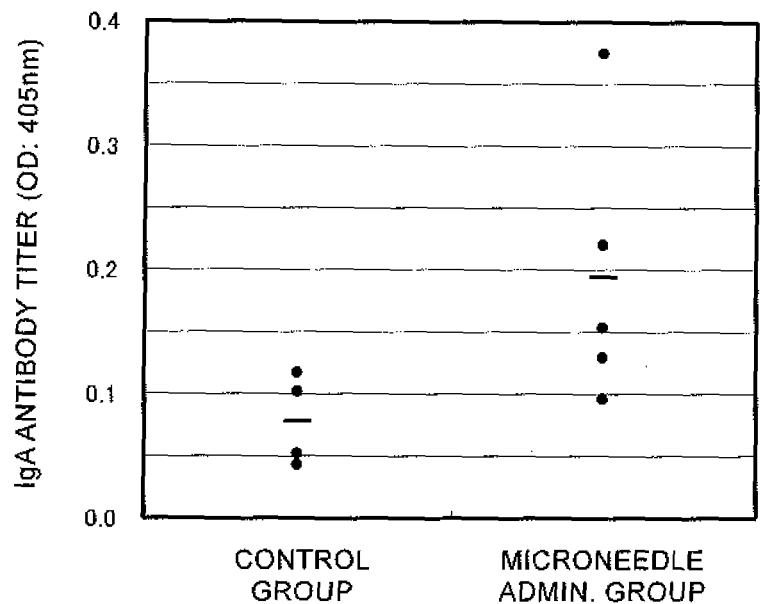
FIG. 3 is a graph showing a comparison between a control group and a microneedle administration group for the IgA antibody titer (nasal cavity).
Figure 4:
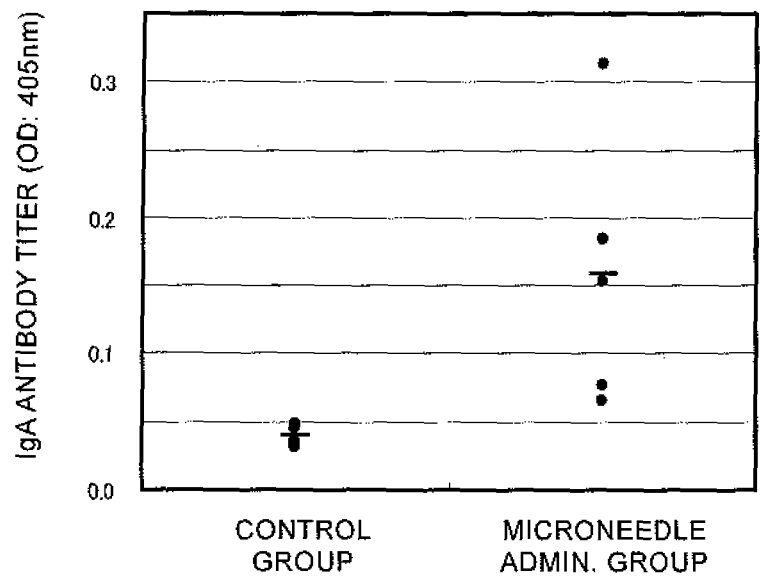
FIG. 4 is a graph showing a comparison between a control group and a microneedle administration group for the IgA antibody titer (lungs).

Subsequently, the plate was washed with 300 µL/well of wash buffer three times, to which a diluted HRP-labeled anti-mouse IgA antibody was added in an amount of 100 µL/well, and the reaction was allowed to proceed at 37° C. for one hour. Then, the plate was washed with 300 µL/well of buffer three times, after which a solution of ABTS peroxidase substrate was added in an amount of 100 µL/well. The reaction was allowed to proceed in the dark at room temperature for 30 minutes, after which a peroxidase stop solution was added in an amount of 100 µL/well to terminate the reaction. Absorbance at 405 nm was then measured.
Coating buffer; 0.05M carbonate buffer (pH 9.5)
Wash buffer; 0.05% Tween20-containing PBS (PBS-T)
Blocking buffer; 1% BSA-containing PBS
Dilution buffer; 1% BSA-containing PBS-T A comparison between a microneedle administration group and a subcutaneous administration group for the IgG antibody titer is shown in FIG. 2. Also, comparisons between a control group, in which the antigen was not administered, and a microneedle administration group for the IgA antibody titer are each shown in FIG. 3 (nasal cavity) and FIG. 4 (lungs).

Experimental Example 4

An influenza HA vaccine containing an antigen having type A strain (H1N1) as an active ingredient that was prepared as described below was concentrated by centrifugation using BIOMAX-10K (manufactured by Millipore). The influenza HA vaccine thus concentrated was mixed with a high molecular weight polymer (pullulan), and the resulting mixture was coated on microneedles made of polylactic acid (a height of approximately 300 a density of 841 needles/cm², in a square pyramid shape) under the condition of a relative humidity of 90 to 1000 RH in a content of 0.3 µg/patch or 3 µg/patch.

The abdominal hair of 4-week-old ddY mice (female) was shaven, and the mice were administered with the microneedles for two hours via skin puncture under anesthesia. The control mice were administered with the same dose (0.3 or 3 µg HA/head) subcutaneously and intracutaneously. After three weeks, the mice were given booster vaccination under the same conditions, and another two weeks after that, the blood was drawn and the HI antibody titer was measured.

Figure 7:
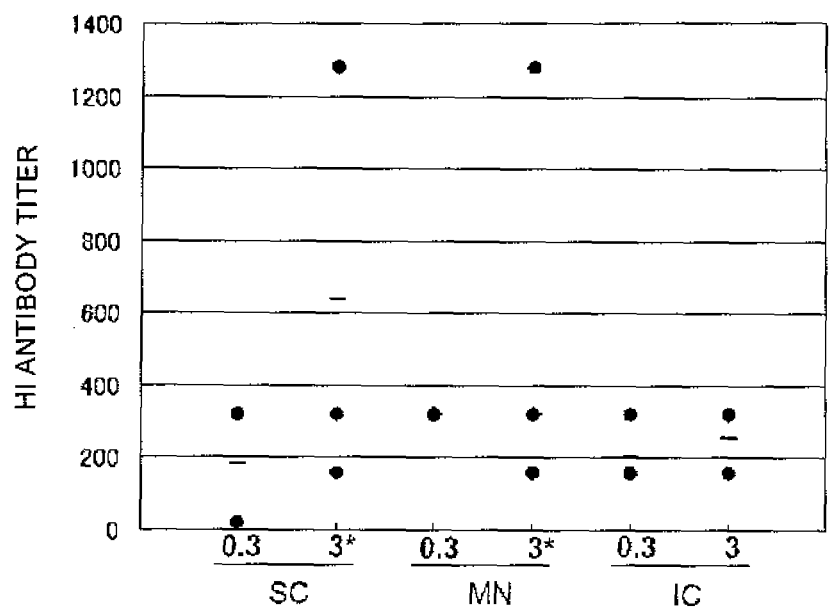
FIG. 7 is a graph showing an example of the measurement results of the HI antibody titer.

FIG. 7 is a graph showing an example of the measurement results of the HI antibody titer. It was found that an antibody titer equivalent to or more than that achieved with subcutaneous administration (SC) was exhibited in both of the groups administered with 0.3 and 3 µg HA/head using the microneedles (MN). An antibody titer equivalent to that achieved with intracutaneous administration (IC) was exhibited in a group administered with 3 µg HA/head. All the mice in a group given an subcutaneous administration of 3 µg HA/head exhibit an antibody titer sufficient to exhibit a defense response. Meanwhile, in a group administered with 0.3 µg HA/head, one mouse was observed to exhibit a low HI antibody titer (20).

The present invention encompasses the followings.

(1) A microneedle device comprising a plurality of microneedles, wherein the microneedles are made of polylactic acid, capable of puncturing skin, arranged two-dimensionally on a base, and coated with an influenza virus antigen comprising a type A strain and a type B strain.
(2) The microneedle device according to the aforementioned (1), wherein the microneedle is in a conical or pyramid shape.
(3) The microneedle device according to the aforementioned (1) or (2), wherein the coating comprises pullulan as a coating carrier.
(4) The microneedle device according to any of the aforementioned (1) to (3), wherein the coating is given at a relative humidity of 70.0 to 100% RH at room temperature.
(5) The microneedle device according to any of the aforementioned (1) to (4), wherein the coating comprises a substance having an adjuvant activity.
(6) The microneedle device according to the aforementioned (5), wherein the substance having an adjuvant activity is lauryl alcohol.
(7) The microneedle device according to any of the aforementioned (1) to (6), wherein the base of the microneedle device comprises a plurality of openings capable of delivering an influenza virus antigen liquid or an influenza virus antigen-dissolving solution.
(8) The microneedle device according to any of the aforementioned (1) to (7), wherein the microneedle has a height of 200 to 500 µm.
(9) The microneedle device according to any of the aforementioned (1) to (8), wherein the microneedles are arranged at a density of 400 to 1000 needles/cm$^2$.
(10) A method for enhancing the efficacy of an influenza vaccine using a microneedle device comprising a plurality of microneedles, wherein the microneedles are made of polylactic acid, capable of puncturing skin, arranged two-dimensionally on a base, and coated with an influenza virus antigen comprising a type A strain and a type B strain.
(11) The method for enhancing the efficacy of an influenza vaccine using a microneedle device according to the aforementioned (10), wherein an administration time of the microneedle device is between 4 minutes to 180 minutes.
(12) The method for enhancing the efficacy of an influenza vaccine using a microneedle device according to the aforementioned (10) or (11), wherein the microneedle is in a conical or pyramid shape.
(13) The method for enhancing the efficacy of an influenza vaccine using a microneedle device according to any of the aforementioned (10) to (12), wherein the coating comprises pullulan as a coating carrier.
(14) The method for enhancing the efficacy of an influenza vaccine using a microneedle device according to any of the aforementioned (10) to (13), wherein the coating is given at a relative humidity of 70.0 to 100 RH at room temperature.
(15) The method for enhancing the efficacy of an influenza vaccine using a microneedle device according to any of the aforementioned (10) to (14), wherein the coating comprises a substance having an adjuvant activity.
(16) The method for enhancing the efficacy of an influenza vaccine using a microneedle device according to the aforementioned (15), wherein the substance having an adjuvant activity is lauryl alcohol.
(17) The method for enhancing the efficacy of an influenza vaccine using a microneedle device according to any of the aforementioned (10) to (16), wherein the base of the microneedle device comprises a plurality of openings capable of delivering an influenza virus antigen liquid or an influenza virus antigen-dissolving solution.
(18) The method for enhancing the efficacy of an influenza vaccine using a microneedle device according to any of the aforementioned (10) to (17), wherein the microneedle has a height of 200 to 500 µm.
(19) The method for enhancing the efficacy of an influenza vaccine using a microneedle device according to any of the aforementioned (10) to (18), wherein the microneedles are arranged at a density of 400 to 1000 needles/cm$^2$.

INDUSTRIAL APPLICABILITY

With use of a microneedle device, the present invention can efficiently and simply increase the immunogenicity of the subtypes of all three strains contained in an influenza vaccine composed of an antigen having type A strain (H1N1), type A strain (H3N2), and type B strain as active ingredients. Hence, the present invention is industrially applicable.

REFERENCE SIGNS LIST

1 Coating
5 Microneedle device
6 Microneedle
7 Opening
8 Microneedle base

The invention claimed is:

1. A method for enhancing the efficacy of an influenza vaccine using a microneedle device for increasing IgG antibody titer and IgA antibody titer in a patient in need thereof comprising applying an adjuvant containing lauryl alcohol to an administration site after administering the influenza vaccine, wherein the microneedle device comprises a plurality of microneedles, and the microneedles are made of polylactic acid, capable of puncturing skin, arranged two-dimensionally on a base, and coated with a coating comprising an influenza virus antigen comprising a type A strain and a type B strain and pullulan as a coating carrier, wherein the method comprises the step of increasing IgG antibody titer and IgA antibody titer in a patient in need thereof.

2. The method for enhancing the efficacy of an influenza vaccine using a microneedle device according to claim 1, wherein an administration time of the microneedle device is between 4 minutes to 180 minutes.

3. The method for enhancing the efficacy of an influenza vaccine using a microneedle device according to claim 1, wherein the microneedle is in a conical or pyramid shape.

4. The method for enhancing the efficacy of an influenza vaccine using a microneedle device according to claim 1, wherein the coating is given at a relative humidity of 70.0 to 100% RH at room temperature.

5. The method for enhancing the efficacy of an influenza vaccine using a microneedle device according to claim 1, wherein the base of the microneedle device comprises a plurality of openings capable of delivering an influenza virus antigen liquid or an influenza virus antigen-dissolving solution.

6. The method for enhancing the efficacy of an influenza vaccine using a microneedle device according to claim 1, wherein the microneedle has a height of 200 to 500 µm.

7. The method for enhancing the efficacy of an influenza vaccine using a microneedle device according to claim 1, wherein the microneedles are arranged at a density of 400 to 1000 needles/cm$^2$.

8. The method for enhancing the efficacy of an influenza vaccine using a microneedle device according to claim 2, wherein an administration time of the microneedle device is between 4 minutes to 10 minutes.

9. A method for enhancing the efficacy of an influenza vaccine using a microneedle device comprising applying an adjuvant containing lauryl alcohol to an administration site after administering the influenza vaccine, wherein the microneedle device comprises a plurality of microneedles, and the microneedles are made of polylactic acid, capable of puncturing skin, arranged two-dimensionally on a base, and coated with a coating comprising an influenza virus antigen comprising a type A strain and a type B strain and pullulan as a coating carrier, wherein the dosage of each antigen in the coating is 0.3 µg/ microneedle device.

\* \* \* \* \*